(12) United States Patent
Tanaka et al.

(10) Patent No.: US 8,933,100 B2
(45) Date of Patent: Jan. 13, 2015

(54) PAROXETINE DERIVATIVE

(71) Applicant: Eisai R&D Management Co., Ltd., Tokyo (JP)

(72) Inventors: Keigo Tanaka, Tsukuba (JP); Tomoki Nishioka, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 128 days.

(21) Appl. No.: 13/752,638

(22) Filed: Jan. 29, 2013

(65) Prior Publication Data

US 2013/0197033 A1 Aug. 1, 2013

Related U.S. Application Data

(60) Provisional application No. 61/592,896, filed on Jan. 31, 2012.

(51) Int. Cl.
*A61K 31/4525* (2006.01)
*C07D 405/12* (2006.01)

(52) U.S. Cl.
CPC .................................... *C07D 405/12* (2013.01)
USPC .......................................... 514/320; 546/196

(58) Field of Classification Search
USPC .......................................... 514/320; 546/196
See application file for complete search history.

(56) References Cited

U.S. PATENT DOCUMENTS

| 4,007,196 A | 2/1977 | Christensen et al. |
| 2007/0191432 A1 | 8/2007 | Tung |

FOREIGN PATENT DOCUMENTS

| WO | 98/056787 | 12/1998 |
| WO | 2007/016431 | 2/2007 |

OTHER PUBLICATIONS

Search Report dated May 7, 2013 for PCT App. Ser. No. PCT/JP2013/051858, 7 pages.

Bertelsen et al., "Apparent mechanism-based inhibition of human CYP2D6 in vitro by paroxetine: comparison with fluoxetine and quinidine," *Drug Metab Dispos.*, Mar. 2003, 31(3):289-293.

Blagg, "Structural alerts for toxicity", Burger's Medicinal Chemistry, Drug Discovery and Development, 7th Edition, edited by Abraham and Rotella, Aug. 2010, pp. 301-334.

Fontana et al., "Cytochrome p450 enzymes mechanism based inhibitors: common sub-structures and reactivity," *Curr Drug Metab.* Oct. 2005, 6(5):413-454.

Lewell et al., "Drug rings database with web interface. A tool for identifying alternative chemical rings in lead discovery programs.", *J Med Chem.*, Jul. 2003, 46(15):3257-3274.

Meanwell, "Synopsis of some recent tactical application of bioisosteres in drug design.", *J Med Chem.*, Apr. 2011, 54(8):2529-2591.

Murray et al., "Selectivity in the inhibition of mammalian cytochromes P-450 by chemical agents," *Pharmacol Rev.* Jun. 1990, 42(2):85-101.

International Preliminary Report on Patentability in WO Patent App. Ser. No. PCT/JP2013/051858, mailed Aug. 14, 2014, 5 pages (with English translation).

*Primary Examiner* — Charanjit Aulakh
(74) *Attorney, Agent, or Firm* — Fish & Richardson P.C.

(57) ABSTRACT

A compound represented by Formula (1), or a pharmacologically acceptable salt thereof retains the principal therapeutic effect of paroxetine and has an improved CYP inhibitory effect:

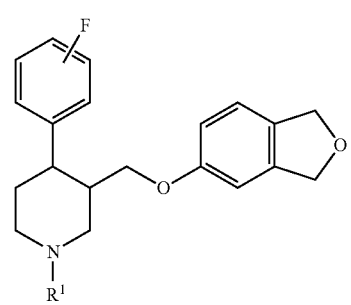

(1)

wherein $R^1$ is a hydrogen atom or $C_{1-6}$ alkyl group.

11 Claims, 1 Drawing Sheet

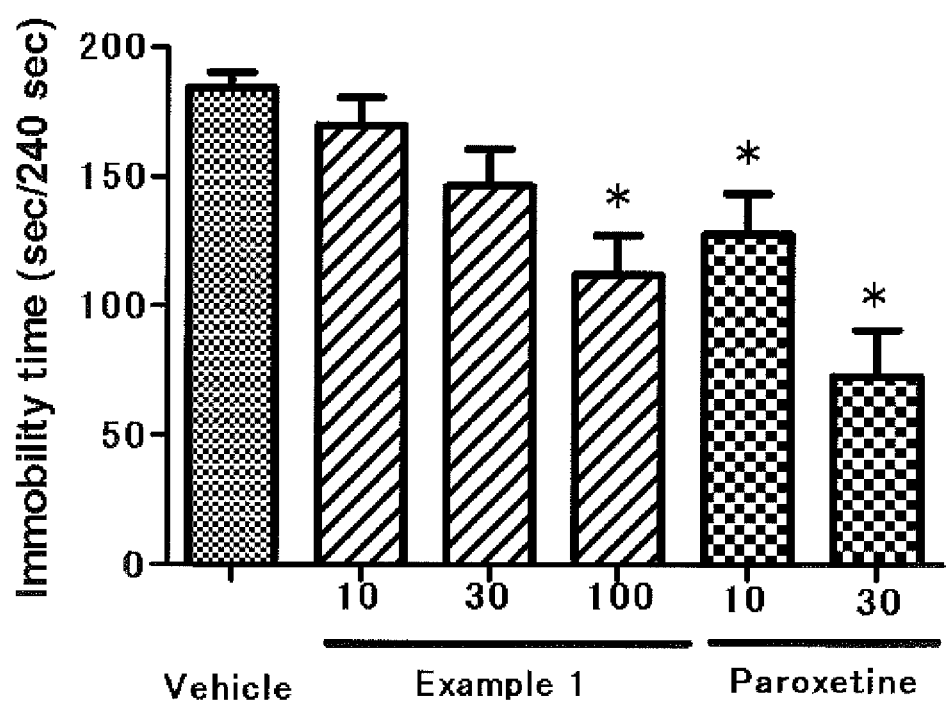

PAROXETINE DERIVATIVE

CROSS-REFERENCE TO RELATED APPLICATION

This application claims the benefit of U.S. provisional application No. 61/592,896 filed on Jan. 31, 2012, the disclosure of which is herein incorporated by reference in its entirety.

TECHNICAL FIELD

The present invention relates to a compound having a phthalan ring. More specifically, it relates to a 3-[(1,3-dihydro-2-benzofuran-5-yloxy)methyl]-4-(fluorophenyl)piperidine compound.

BACKGROUND ART

3-[(2H-1,3-benzodioxol-5-yloxy)methyl]-4-phenylpiperidine compounds are known as selective serotonin reuptake inhibitors. For example, paroxetine, also known as (3S,4R)-3-[(2H-1,3-benzodioxol-5-yloxy)methyl]-4-(4-fluorophenyl)piperidine, is widely used as an anti-depressant agent (Patent Literature 1).

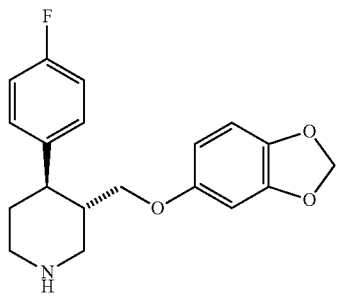

Paroxetine

However, the structure of paroxetine includes a benzodioxol ring, and in general, compounds having such benzodioxol rings are converted to chemically highly reactive metabolites when metabolized by cytochrome P450 (CYP), and are known to irreversibly inhibit the activity of CYP by inactivation based on the covalent binding with CYP (Non Patent Literatures 1-3). In fact, paroxetine is reported to cause drug-drug interactions by inhibiting the CYP-mediated metabolism of several drugs that are co-administered with it clinically, and some of these are contraindicated. To solve this problem, a compound has been developed having a deuterium atom substituted for a hydrogen atom on the methylene carbon of the benzodioxolyl group of paroxetine, but no such compound is yet in commercial use, and the effects have been unsatisfactory (Patent Literature 2). Also, it is known that compounds containing deuterium generally require higher production costs. As a consequence, to solve this problem there is a need for a method that does not use deuterium.

CITATION LIST

[Patent Literature 1] U.S. Pat. No. 4,007,196
[Patent Literature 2] U.S. Patent Application Publication No. 2007/0191432
[Non Patent Literature 1] Pharmacological reviews 42, 85, 1990 (Selectivity in the inhibition of Mammalian Cytochrome P-450 by Chemical Agents)
[Non Patent Literature 2] Current Drug Metabolism, 6, 413, 2005
[Non Patent Literature 3] Drug Metabolism and Disposition 31, 289, 2003
[Non Patent Literature 4] Burger's Medicinal Chemistry, Drug Discovery and Development, 7th Edition, edited by Abraham and Rotella, August 2010, "STRUCTURAL ALERTS FOR TOXICITY" by Blagg, p 301-334
[Non Patent Literature 5] J Med Chem, 54, 2529-2591, 2011
[Non Patent Literature 6] J Med Chem, 46, 3257-3274, 2003

SUMMARY OF INVENTION

Technical Problem

It is an object of the present invention to provide a compound retaining the principal therapeutic effect of paroxetine and having an improved CYP inhibitory effect as well as having a structure that contains no deuterium.

Solution to Problem

As a result of intensive studies, the present inventors have found the present invention. Specifically, the present invention relates to the following [1] to [17]

[1] A compound represented by formula (1), or a pharmacologically acceptable salt thereof:

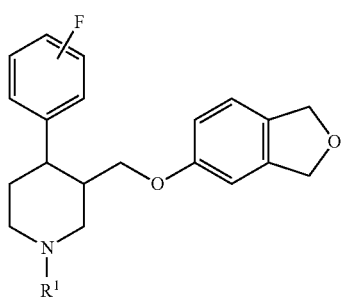

(1)

wherein $R^1$ is a hydrogen atom or $C_{1-6}$ alkyl group.

[2] The compound or pharmacologically acceptable salt thereof according to [1], wherein $R^1$ is a hydrogen atom.

[3] The compound or pharmacologically acceptable salt thereof according to [1] or [2], wherein the fluorine atom is attached at the para-position with respect to the piperidine ring.

[4] (3S,4R)-3-[(1,3-Dihydro-2-benzofuran-5-yloxy)methyl]-4-(4-fluorophenyl) piperidine or a pharmacologically acceptable salt thereof.

[5] A pharmaceutical composition comprising the compound or pharmacologically acceptable salt thereof according to any one of [1] to [4].

[6] The pharmaceutical composition according to [5], which is a selective serotonin reuptake inhibitor.

[7] The pharmaceutical composition according to [5], which is an antidepressant agent.

[8] The pharmaceutical composition according to [5], which is an agent for the treatment or prevention of premature ejaculation.

[9] A method of selectively inhibiting serotonin reuptake comprising administering the compound or pharmacologically acceptable salt thereof according to any one of [1] to [4] to a patient.

[10] A method of treating or preventing depression comprising administering the compound or pharmacologically acceptable salt thereof according to any one of [1] to [4] to a patient.

[11] A method of treating or preventing premature ejaculation comprising administering the compound or pharmacologically acceptable salt thereof according to any one of [1] to [4] to a patient.

[12] A compound or pharmacologically acceptable salt thereof according to any one of [1] to [4] for use for selectively inhibiting serotonin reuptake.

[13] A compound or pharmacologically acceptable salt thereof according to any one of [1] to [4] for use for treating or preventing depression.

[14] A compound of pharmacologically acceptable salt thereof according to any one of [1] to [4] for use for treating or preventing premature ejaculation.

[15] Use of the compound or pharmacologically acceptable salt thereof according to any one of [1] to [4] for the manufacture of a selective serotonin reuptake inhibitor.

[16] Use of the compound or pharmacologically acceptable salt thereof according to any one of [1] to [4] for the manufacture of an antidepressant agent.

[17] Use of the compound or pharmacologically acceptable salt thereof according to any one of [1] to [4] for the manufacture of an agent for the treatment or prevention of premature ejaculation.

Advantageous Effects of Invention

The compound represented by formula (1) (hereunder called Compound (1)) retains the principal therapeutic effect of paroxetine and having an improved CYP inhibitory effect compared to paroxetine.

BRIEF DESCRIPTION OF DRAWINGS

FIG. 1 is a graph showing the effects of the compound of Example 1 and paroxetine on rest time in a mouse forced swimming test. Results are expressed as mean±S.E.M. of 8-9 mice. *p<0.05 vs. vehicle control

DESCRIPTION OF EMBODIMENTS

The present invention will be described in detail below.

In the present specification, the present invention is not limited to a particular crystal form but may include any one of crystal forms or mixtures thereof, although crystal polymorphs may exist. The present invention also includes amorphous forms, and the compounds according to the present invention include anhydrides and hydrates.

The meanings of the terms, symbols and the like used in the present specification are explained below, and the present invention is explained in detail.

"CYP" in the present specification is the drug-metabolizing enzyme Cytochrome P450.

"Improve CYP inhibitory effect" or "improved CYP inhibitory effect" in the present specification means that the degree of inhibition of one or two among five CYP molecules (CYP1A2, 2C9, 2C19, 2D6 and 3A4), the major CYP molecules, is generally improved than that of paroxetine.

"Retains the principal therapeutic effect" in the present specification means that showing in vitro or in vivo pharmacological activity in preclinical study, which is expected to show clinical therapeutic effect as paroxetine does. In vitro pharmacological activity means, for example, inhibitory activity on serotonin transporter, and in vivo pharmacological activity means, for example, pharmacological activity based on a forced swimming test.

"$IC_{50}$" in the present specification means the 50% inhibition concentration or half inhibition concentration.

The "$C_{1-6}$ alkyl group" in the present specification means a linear or branched alkyl group having 1 to 6 carbon atoms, and examples include a methyl group, an ethyl group, a 1-propyl group, a 2-propyl group, a 2-methyl-1-propyl group, a 2-methyl-2-propyl group, a 1-butyl group, a 2-butyl group, a 1-pentyl group, a 2-pentyl group, a 3-pentyl group, a 1-hexyl group, a 2-hexyl group and a 3-hexyl group.

The "benzodioxol ring" in the present specification is a ring or functional group having the following structure:

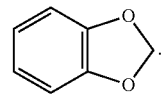

The "phthalan ring" in the present specification means a ring or functional group having the following structure:

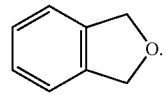

The "pharmacologically acceptable salt" in the present specification is not particularly limited insofar as it forms a salt with the compound represented by formula (1) and is pharmacologically acceptable, and examples include inorganic acid salts, organic acid salts, inorganic base salts, organic base salts, and acidic or basic amino acid salts.

Preferred examples of inorganic acid salts include hydrochlorides, hydrobromides, sulfates, nitrates and phosphates, and preferred examples of organic acid salts include acetates, succinates, fumarates, maleates, tartrates, citrates, lactates, stearates, benzoates, mandelates, methanesulfonates, ethanesulfonates, p-toluenesulfonates and benzenesulfonates.

Preferred examples of inorganic base salts include alkali metal salts such as sodium salts and potassium salts, alkaline earth metal salts such as calcium salts and magnesium salts, aluminum salts and ammonium salts, and preferred examples of organic base salts include diethylamine salts, diethanolamine salts, meglumine salts and N,N'-dibenzylethylenediamine salts.

Preferred examples of acidic amino acid salts include aspartates and glutamates, and preferred examples of basic amino acid salts include arginine salts, lysine salts and ornithine salts.

The compound represented by formula (1) can be produced by the methods described below, or by the method described below with improvements made by a person skilled in the art based on ordinary knowledge. However, the method of producing the compound represented by formula (1) is not limited to these.

Process A

When $R^1$ of Compound (1) is a $C_{1-6}$ alkyl group, Compound (1) can be obtained by the following Process A:

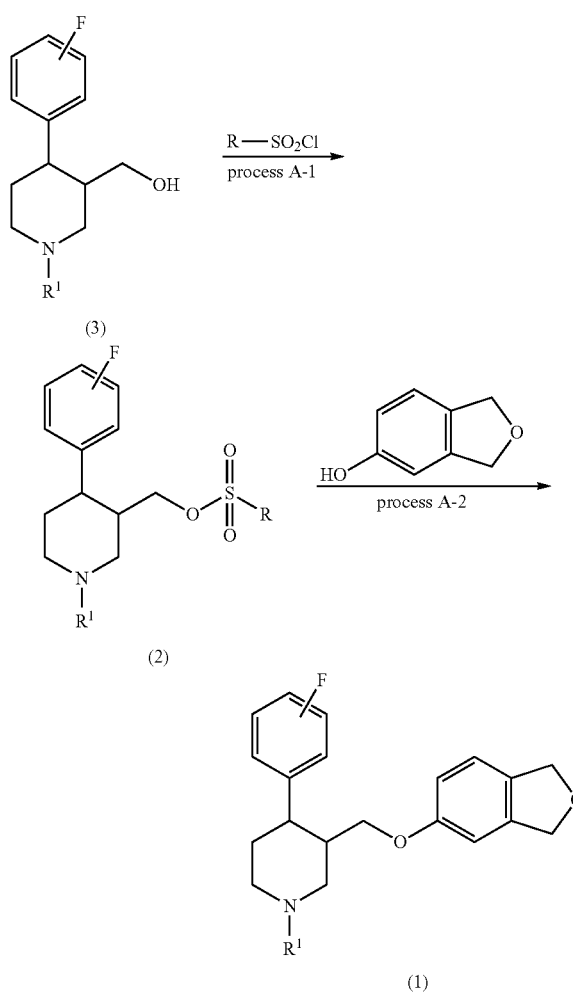

(3)

(2)

(1)

In the scheme, R is a $C_{1-6}$ alkyl group or a phenyl group optionally substituted with a $C_{1-6}$ alkyl group, and $R^1$ is a hydrogen atom or a $C_{1-6}$ alkyl group; however, $R^1$ in Process A is a $C_{1-6}$ alkyl group.

Process A-1 is a method of obtaining Compound (2) by reacting Compound (3) with a sulfonic acid esterification agent in an inert solvent in the presence of a base.

Examples of sulfonic acid esterification agents include methanesulfonyl chloride, benzenesulfonyl chloride and p-toluenesulfonyl chloride, and methanesulfonyl chloride is preferred.

The solvent used is not particularly limited as long as it dissolves the starting materials to a certain extent without inhibiting the reaction, but examples include ethers such as tetrahydrofuran, halogenated hydrocarbons such as dichloromethane and chloroform, and aromatic hydrocarbons such as benzene and toluene, with dichloromethane and toluene being preferred.

The base used may be triethylamine, diisopropylethylamine or the like, with triethylamine being preferred.

The reaction temperature differs according to the starting materials, the solvent and the base, but is normally −20° to 100° C., and preferably 0° C. to 60° C.

The reaction time differs according to the starting materials, the solvent and the base, but is normally 10 minutes to 3 days, and preferably 30 minutes to 1 day.

Process A-2 is a method of obtaining Compound (1) by reacting Compound (2) with 1,3-dihydro-2-benzofuran-5-ol in an inactive solvent in the presence of a base.

The solvent used is not particularly limited as long as it dissolves the starting materials to a certain extent without inhibiting the reaction, but examples include amides such as N,N-dimethylformamide, N,N-dimethylacetamide and 1-methylpyrrolidinone, ethers such as tetrahydrofuran, and sulfoxides such as dimethylsulfoxide, with N,N-dimethylformamide being preferred.

The base used may be a base such as organic lithium or sodium hydride, with sodium hydride being preferred.

The reaction temperature differs according to the starting materials, the solvent and the base, but is normally −20° to 100° C., or preferably 0° C. to 100° C.

The reaction time differs according to the starting materials, the solvent and the base, but is normally 10 minutes to 3 days, or preferably 30 minutes to 1 day.

Process B

When the $R^1$ of Compound (1) is a hydrogen atom, Compound (I) can be obtained by the following Process B.

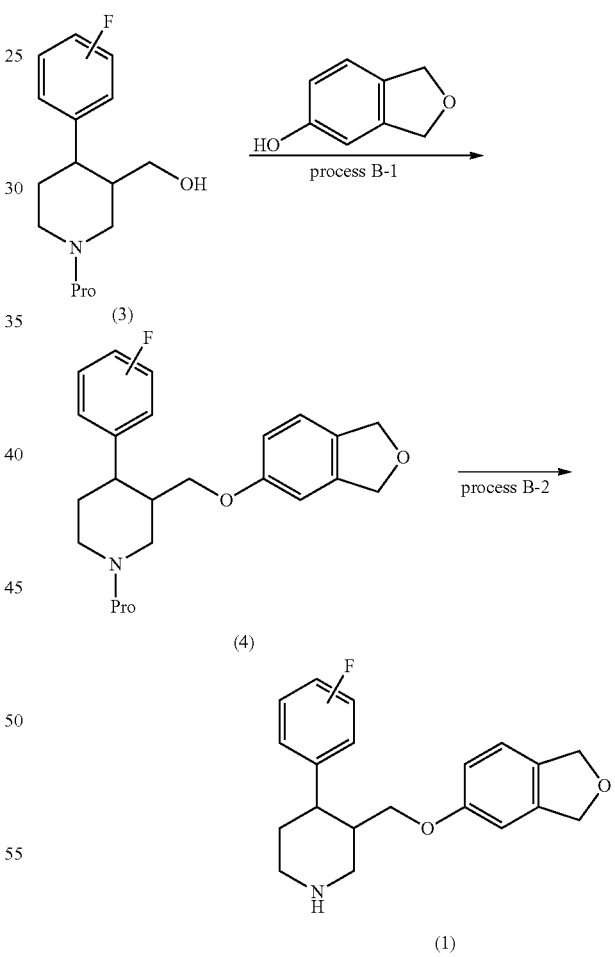

(3)

(4)

(1)

wherein Pro is a protecting group of the amine.

Process B-1 is a method similar to the synthesis method described for Step A above. The protecting group of the amine may be t-butyloxycarbonyl, benzyloxycarbonyl or p-toluenesulfonyl group or the like.

Process B-2 is a step of deprotecting the protecting group of the amine to obtain a secondary amine.

The amine may be deprotected by known methods, and when the protecting group is a t-butyloxycarbonyl group for example, deprotection can be accomplished by treatment with an acid such as trifluoroacetic acid.

After completion of the reaction in each process of each method described above, the target compound in each process can be collected from the reaction mixture according to a conventional method.

For example, when the whole reaction mixture is a liquid, the reaction mixture is cooled to room temperature or cooled with ice as desired, and neutralized with an acid, alkali, oxidizing agent or reducing agent as appropriate, an organic solvent immiscible with water and not reactive with the target compound such as ethyl acetate is added, and the layer containing the target compound is separated. Next, a solvent immiscible with the resulting layer and not reactive with the target compound is added, the layer containing the target compound is washed, and the layer is separated. Moreover, when the layer is an organic layer, the target compound can be collected by drying with a drying agent such as anhydrous magnesium sulfate or anhydrous sodium sulfate and distilling off the solvent. When the layer is an aqueous layer, the target compound can be collected by electrically demineralizing and then lyophilizing the layer.

In addition, when the whole reaction mixture is a liquid and if possible, the target compound can be collected only by distilling off substances other than the target compound (such as a solvent or a reagent) under normal pressure or reduced pressure.

Further, when only the target compound is precipitated as a solid, or when the whole reaction mixture described above is a liquid and only the target compound is precipitated in the course of collection, the target compound can be further collected by collecting the target compound by filtration first, washing the target compound collected by filtration with an appropriate organic or inorganic solvent and drying, such that the mother liquor is treated in a manner similar to the case where the whole reaction mixture described above is a liquid.

Still further, when only the reagent or catalyst is present as a solid, or the whole reaction mixture described above is a liquid and only the reagent or catalyst is precipitated as a solid in the course of collection, and the target compound is dissolved in the solution, the target compound can be collected by filtering off the reagent or catalyst first, washing the reagent or catalyst filtered off with an appropriate organic or inorganic solvent, combining the resulting washings with the mother liquor, and treating the resulting mixture in a manner similar to the case where the whole reaction mixture described above is a liquid.

In particular, when substances other than the target compound which are contained in the reaction mixture do not inhibit the reaction in the next step, the reaction mixture may also be used in the next step as is without particularly isolating the target compound.

Recrystallization, various chromatography methods and distillation may be carried out as appropriate in order to improve the purity of the target compound collected by the above method.

Typically, when the collected target compound is a solid, the purity of the target compound can be improved by recrystallization. In recrystallization, a single solvent or a mixture of a plurality of solvents not reactive with the target compound may be used. Specifically, the target compound is first dissolved in one or more solvents not reactive with the target compound at room temperature or under healing. The resulting mixture is cooled with ice water or the like or is stirred or left to stand at room temperature, such that the target compound can be crystallized from the mixture.

The purity of the collected target compound can be improved by various chromatography methods. Generally, it is possible to use weak acidic silica gels such as Silica gel 60 manufactured by Merck KGaA (70-230 mesh or 340-400 mesh) and BW-300 manufactured by Fuji Silysia Chemical Ltd. (300 mesh). When the target compound is basic and is adsorbed onto the above silica gels too strongly, it is also possible to use NH silica gels such as propylamine coated silica gel manufactured by Fuji Silysia Chemical Ltd. (200-350 mesh) and disposable medium pressure preparative packed column manufactured by Yamazen Corporation (Hi-Flash Amino). When the target compound is dipolar or must be eluted with a more polar solvent such as methanol, for example, it is also possible to use NAM-200H or NAM-300H manufactured by NAM Laboratory or YMC GEL ODS-A manufactured by YMC Co. Ltd. It is also possible to use disposable medium pressure preparative packed columns as described above that are previously packed with fillers and manufactured by Yamazen Corporation, Wako Pure Chemical Industries, Ltd., Biotage AB or W. R. Grace & Co. (Hi-Flash). The target compound whose purity is improved can be obtained by eluting the target compound with one or more solvents not reactive with the target compound using these silica gels, and distilling off the solvent(s).

When the collected target compound is a liquid, the purity of the target compound can also be improved by distillation. In distillation, the target compound can be distilled out by subjecting the target compound to reduced pressure at room temperature or under heating.

Representative examples of the method for producing Compound (1) have been described above. Raw material compounds and various reagents in the production of Compound (1) may form salts or solvates such as hydrates, all vary depending on the starting material, the solvent used or the like, and are not particularly limited insofar as they do not inhibit the reaction. Also, the solvent used varies depending on the starting material, the reagent or the like, and is not particularly limited insofar as it does not inhibit the reaction and dissolves the starting material to some degree, obviously. When Compound (1) is obtained as free form, it can be converted to a salt that may be formed by Compound (1) or solvate of the compound or salt by conventional methods.

When Compound (1) is obtained as a salt or solvate, it can be converted to free form of Compounds (1) by conventional methods.

Various isomers obtained for Compound (1) (such as geometric isomers, optical isomers, rotamers, stereoisomers and tautomers) can be purified and isolated using common separation means, for example, recrystallization, diastereomeric salt formation, enzymatic resolution and various chromatography methods (such as thin layer chromatography, column chromatography and gas chromatography).

Compound (1) or a pharmacologically acceptable salt thereof can be formulated by conventional methods, and examples of dosage forms include oral formulations (such as tablets, granules, powders, capsules and syrups), injections (for intravenous administration, intramuscular administration, subcutaneous administration and intraperitoneal administration) and external formulations (such as transdermal absorption formulations (such as ointments and patches), ophthalmic preparations, nasal preparations and suppositories).

These solid formulations such as tablets, capsules, granules and powders may contain usually 0.001 to 99.5 wt %, preferably 0.01 to 90 wt % or the like, of Compound (1) or a pharmacologically acceptable salt thereof.

When oral solid formulations are manufactured, tablets, granules, powders and capsules can be prepared by adding diluents, binders, disintegrants, lubricants, colorants or the like to Compound (1) or a pharmacologically acceptable salt thereof as necessary and treating by conventional methods. Tablets, granules, powders, capsules and the like may also be film coated as necessary.

Examples of diluents include lactose, corn starch and microcrystalline cellulose, examples of binders include hydroxypropylcellulose and hydroxypropylmethylcellulose, and examples of disintegrants include carboxymethylcellulose calcium and croscarmellose sodium.

Examples of lubricants include magnesium stearate and calcium stearate, and examples of colorants include titanium oxide.

Examples of film coating agents include hydroxypropylcellulose, hydroxypropylmethylcellulose and methylcellulose.

Any excipients described above are not limited to these examples, obviously.

When injections (for intravenous administration, intramuscular administration, subcutaneous administration and intraperitoneal administration) are manufactured, they can be manufactured by adding pH adjusters, buffers, suspending agents, solubilizing agents, antioxidants, preservatives (antiseptics), tonicity adjusting agents or the like to Compound (1) or a pharmacologically acceptable salt thereof as necessary and treating by conventional methods. Lyophilized formulations to be dissolved before use may also be prepared by lyophilization. These injections can be administered intravenously, subcutaneously and intramuscularly, for example.

Examples of pH adjusters and buffers include organic acids or inorganic acids and/or salts thereof examples of suspending agents include methylcellulose, polysorbate 80 and carboxymethylcellulose sodium, examples of solubilizing agents include polysorbate 80 and polyoxyethylene sorbitan monolaurate, examples of antioxidants include α-tocopherol, examples of preservatives include methyl parahydroxybenzoate and ethyl parahydroxybenzoate, and examples of tonicity adjusting agents include glucose, sodium chloride and mannitol; however, the excipients are not limited to these examples, obviously.

These injections may contain usually 0.000001 to 99.5 wt %, preferably 0.00001 to 90 wt % or the like, of Compound (1) or a pharmacologically acceptable salt thereof.

When external formulations are manufactured, transdermal absorption formulations (such as ointments and patches), ophthalmic preparations, nasal preparations, suppositories and the like can be manufactured by adding base materials and, as necessary, the emulsifiers, preservatives, pH adjusters, colorants and the like described above to Compound (1) or a pharmacologically acceptable salt thereof, and treating by conventional methods.

Various raw materials conventionally used for pharmaceuticals, quasi drugs, cosmetics and the like can be used as base materials, and examples include raw materials such as animal and vegetable oils, mineral oils, ester oils, waxes, higher alcohols and purified water.

These external formulations may contain usually 0.000001 to 99.5 wt %, preferably 0.00001 to 90 wt % or the like, of Compound (1) or a pharmacologically acceptable salt thereof.

The dosage of the medicine according to the present invention typically varies depending on the symptom, age, sex, weight or the like, but is acceptable if it is a dosage sufficient to produce a desired effect. For example, for an adult, a dosage of about 0.1 to 5000 mg (preferably 0.5 to 1000 mg, more preferably 1 to 600 mg) per day is used in one dose during one or more days or in 2 to 6 divided doses for one day.

Compound (1) can be used as a chemical probe to trap target proteins in bioactive low molecular weight compounds. Specifically, Compound (1) can be converted to an affinity chromatography probe, a photoaffinity probe or the like by introducing a labeling group, a linker or the like into a moiety differing from a structural moiety essential for expression of activity of the compound by a technique described in J. Mass Spectrum. Soc. Jpn., Vol. 51, No. 5, 2003, pp. 492-498 or WO 2007/139149 or the like.

Examples of labeling groups, linkers or the like used for chemical probes include groups shown in the group consisting of (1) to (5) below.

(1) protein labeling groups such as photoaffinity labeling groups (such as a benzoyl group, a benzophenone group, an azido group, a carbonylazido group, a diaziridine group, an enone group, a diazo group and a nitro group) and chemical affinity groups (such as a ketone group in which an α-carbon atom is replaced with a halogen atom, a carbamoyl group, an ester group, an alkylthio group, Michael receptors such as α,β-unsaturated ketones and esters, and an oxirane group), (2) cleavable linkers such as —S—S—, —O—Si—O—, monosaccharides (such as a glucose group and a galactose group) or disaccharides (such as lactose), and oligopeptide linkers cleavable by enzymatic reaction, (3) fishing tag groups such as biotin and a 3-(4,4-difluoro-5,7-dimethyl-4H-3a,4a-diaza-4-bora-s-indacen-3-yl)propionyl group, (4) detectable markers such as radiolabeling groups such as $^{125}$I, $^{32}$P, $^{3}$H and $^{14}$C; fluorescence labeling groups such as fluorescein, rhodamine, dansyl, umbelliferone, 7-nitrofurazanyl and a 3-(4,4-difluoro-5,7-dimethyl-4H-3a,4a-diaza-4-bora-s-indacen-3-yl)propionyl group; chemiluminescent groups such as luciferin and luminol; and heavy metal ions such as lanthanoid metal ions and radium ions; or (5) groups bound to solid phase carriers such as glass beads, glass beds, microtiter plates, agarose beads, agarose beds, polystyrene beads, polystyrene beds, nylon beads and nylon beds.

Probes prepared by introducing labeling groups or the like selected from the group consisting of (1) to (5) above into Compound (1) according to the method described in the above documents or the like can be used as chemical probes for identification of labeled proteins useful for searching for novel drug targets, for example.

EXAMPLES

Compound (1) can be produced for example by the methods described in the following examples, and the effects of Compound (1) can be confirmed by the methods described in the following test examples. These examples are illustrative, however, and the present invention is not specifically restricted the specific examples.

Example 1

(3S,4R)-3-[(1,3-dihydro-2-benzofuran-5-yloxy)methyl]-4-(4-fluorophenyl)piperidine

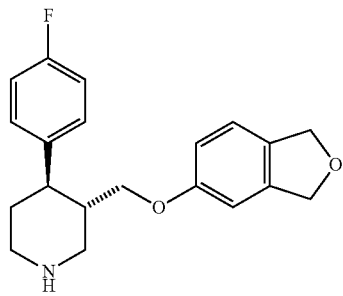

To tert-butyl (3S,4R)-3-[(1,3-dihydro-2-benzofuran-5-yloxy)methyl]-4-(4-fluorophenyl)piperidine-1-carboxylate (4.1 g, 9.6 mmol) described in Production Example 1-4 was added a mixed solution of trifluoroacetic acid (5 mL) and dichloromethane (30 mL) under ice cooling, followed by stirring at room temperature for 90 minutes. Toluene (30 mL) was added to the reaction mixture, and the solvent was distilled away under reduced pressure. The residue was purified by NH silica gel column chromatography (methanol:ethyl acetate=1:20) to give the title compound (2.7 g, 84% yield).

$^1$H-NMR Spectrum (CDCl$_3$) δ (ppm): 1.67-1.77 (1H, m), 1.82 (1H, dq, J=2.6, 6.6 Hz), 2.06-2.14 (1H, m), 2.60 (1H, dt, J=4.0, 11.7 Hz), 2.69 (1H, dd, J=11.3, 12.1 Hz), 2.75 (1H, dt, J=2.9, 12.1 Hz), 3.19 (1H, d, J=3.2 Hz), 3.44 (1H, dd, J=3.7, 12.1 Hz), 3.51 (1H, dd, J=7.1, 9.3 Hz), 3.64 (1H, dd, J=2.9, 9.5 Hz), 5.01 (4H, s), 6.58 (1H, d, J=2.2 Hz), 6.64 (1H, dd, J=2.4, 8.2 Hz), 6.95-7.01 (2H, m), 7.05 (1H, d, J=8.1 Hz), 7.15-7.20 (2H, m).

Production Example 1-1

2-[(prop-2-yn-1-yloxy)methyl]furan

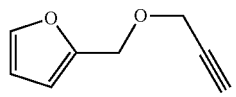

To a mixture of sodium hydride (7.7 g, 190 mmol, 60% in oil) and tetrahydrofuran (100 mL) was added dropwise furfuryl alcohol (15 mL, 170 mmol) at 0° C. The reaction mixture was warmed to room temperature, N,N-dimethylformamide (30 mL) was added at that temperature, and the mixture was stirred at that temperature for 30 minutes. The reaction mixture was returned to 0° C., propargyl bromide (23 g, 190 mmol) was added at that temperature, and the mixture was stirred for 1 hour at room temperature. Water was added to the reaction mixture, which was then extracted with ethyl acetate. The organic layer was washed with brine and the solvent was distilled away under reduced pressure. The residue was purified by silica gel column chromatography (ethyl acetate:heptane=1:30) to give the title compound (7.6 g, 32% yield).

$^1$H-NMR Spectrum (CDCl$_3$) δ (ppm): 2.47 (1H, t, J=2.6 Hz), 4.17 (2H, d, J=2.6 Hz), 4.57 (2H, s), 6.36 (1H, dd, J=1.8, 3.3 Hz), 6.376-6.384 (1H, m), 7.43 (1H, dd, J=0.7, 1.8 Hz).

Production Example 1-2

1,3-dihydro-2-benzofuran-5-ol

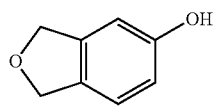

To a mixture of 2-[(prop-2-yn-1-yloxy)-methyl]furan (6.6 g, 49 mmol) described in Production Example 1-1 and acetone (66 ml) was added platinum(II) chloride (650 mg, 2.4 mmol) at room temperature, followed by reflux heating for 5 hours. The reaction mixture was returned to room temperature, and the solvent was distilled away under reduced pressure. The residue was filtered with silica gel (ethyl acetate elution), and the solvent was distilled away under reduced pressure. Dichloromethane (20 mL) was added to the residue, and an insoluble solid was collected by filtration to give the title compound (1.7 g). The filtrate was distilled away under reduced pressure, and the residue was purified by silica gel column chromatography (ethyl acetate:heptane=1:4) to give the title compound (1.6 g, total 3.3 g, 49% yield).

$^1$H-NMR Spectrum (CDCl$_3$) δ (ppm): 5.06 (4H, s), 6.71 (1H, d, J=2.2 Hz), 6.74 (1H, dd, J=2.2, 8.1 Hz), 7.08 (1H, d, J=8.1 Hz).

Production Example 1-3 tert-butyl (3S,4R)-4-(4-fluorophenyl)-3-(hydroxymethyl)piperidine-1-carboxylate

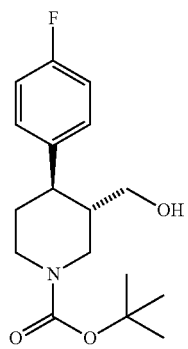

To a mixture of [(3S,4R)-4-(4-fluorophenyl)piperidine-3-yl]methanol (3.0 g, 14 mmol), sodium carbonate (6.1 g, 57 mmol), dichloromethane (40 mL) and water (40 mL) was added di-tert-butyl Bicarbonate (3.8 g, 17 mmol) under ice cooling, followed by stirring at the same temperature for 30 minutes. The reaction mixture was added to a mixed solution of dichloromethane and water, and the organic layer was separated. The organic layer was washed with brine and dried over anhydrous magnesium sulfate, and the solvent was distilled away under reduced pressure. The residue was purified by silica gel column chromatography (ethyl acetate:heptane=1:1) to give the title compound (4.0 g, 90% yield).

$^1$H-NMR Spectrum (CDCl$_3$) δ (ppm): 1.49 (9H, s), 1.61-1.71 (1H, m), 1.75-1.85 (2H, m), 2.51-2.56 (1H, m), 2.71 (1H, dd, J=11.3, 13.2 Hz), 2.78 (1H, br s), 3.24-3.29 (1H, m), 3.42-3.46 (1H, m), 4.20 (1H, br s), 4.36 (1H, d, J=11.7 Hz), 6.97-7.03 (2H, m), 7.13-7.18 (2H, m).

Production Example 1-4 tert-butyl (3S,4R)-3-[(1,3-dihydro-2-benzofuran-5-yloxy)methyl]-4-(4-fluorophenyl)piperidine-1-carboxylate

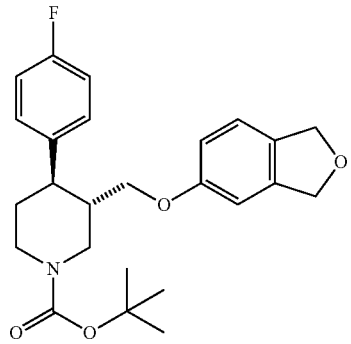

To a mixture of tert-butyl (3S,4R)-4-(4-fluorophenyl)-3-(hydroxymethyl)piperidine-1-carboxylate (3.6 g, 12 mmol) described in Production Example 1-3 and toluene (40 mL) were added triethylamine (2.1 mL, 15 mmol) and methanesulfonyl chloride (0.93 mL, 12 mmol) at 0° C., followed by stirring at room temperature for 30 minutes. Methanesulfonyl chloride (0.11 mL, 1.5 mmol) was further added at the same temperature, and stirred at the same temperature for 30 minutes. Water was added to the reaction mixture, which was then extracted with ethyl acetate. The organic layer was washed with brine and dried over anhydrous magnesium sulfate, and the solvent was distilled away under reduced pressure. tert-Butyl (3S,4R)-4-(4-fluorophenyl)-3-[methanesulfonyloxy)methyl]piperidine-1-carboxylate was obtained as a crude product. To a mixture of 1,3-dihydro-2-benzofuran-5-ol (1.6 g, 12 mmol) described in Production Example 1-2 and N,N-dimethylformamide (50 mL) was added sodium hydride (460 mg, 12 mmol, 60% in oil) at 0° C., followed by stirring at the same temperature for 30 minutes. To this reaction mixture was added a mixture of the crude product of tert-butyl (3S, 4R)-4-(4-fluorophenyl)-3-[methanesulfonyloxy)methyl]piperidine-1-carboxylate and N,N-dimethylformamide (20 mL), followed by stirring at 80° C. for 90 minutes. The reaction mixture was returned to room temperature, and extracted with ethyl acetate after addition of water. The organic layer was washed with brine, and the solvent was distilled away under reduced pressure. The residue was purified by silica gel column chromatography (ethyl acetate:heptane=1:3) to give the title compound (4.7 g, 92% yield).

$^1$H-NMR Spectrum (CDCl$_3$) δ (ppm): 1.50 (9H, s), 1.69-1.83 (2H, m), 2.01-2.09 (1H, m), 2.69 (1H, dt, J=3.7, 11.7 Hz), 2.78-2.84 (2H, m), 3.52 (1H, dd, J=6.6, 9.1 Hz), 3.67 (1H, dd, J=2.9, 9.5 Hz), 4.25 (1H, br s), 4.46 (1H, br s), 5.02 (4H, s), 6.59 (1H, d, J=2.2 Hz), 6.66 (1H, dd, J=2.2, 8.1 Hz), 6.95-7.00 (2H, m), 7.06 (1H, d, J=8.1 Hz), 7.12-7.16 (2H, m).

Test Example 1

Evaluation of Inhibitory Action on Serotonin Transporter

The inhibitor action of the compound of the present invention on serotonin transporter was evaluated using rat platelets expressing serotonin transporters.

That is, the test compound was added to rat platelets, the fluorescent substance of a Neurotransmitter Transporter Activity Assay Kit (Molecular Devices, R8174) was added beginning after 15 minutes, and changes in fluorescent intensity from uptake of the fluorescent substance were measured over time to evaluate the inhibitory effect of the test compound on serotonin transporter.

1 Blood was collected from the rat inferior vena cava under halothane inhalation anesthesia.

2 Centrifugation was carried out at 350 g at room temperature for 5 minutes, and the supernatant containing platelet-rich plasma was collected in 15 ml falcon tubes.

3 Centrifugation was carried out at 2100 g at room temperature for 10 minutes to obtain platelets as a pellet. Ca-free K5 buffer was added in the amount of 0.7 times the amount of platelet-rich plasma obtained in operation 2, and the pellet was triturated by pipetting.

4 The platelet liquid was dispensed 30 μl/well on a 384 plate, and 10 μl of the test compound was then added to each well, and incubated for 15 minutes at room temperature.

5 The fluorescent substance of a Neurotransmitter Transporter Activity Assay Kit was added, and changes in fluorescent intensity over time from uptake of the fluorescent substance through serotonin transporters were measured with a FDSS 6000 (Hamamatsu Photonics).

Pharmacological Evaluation Methods

The serotonin transporter inhibition rate of the test compound was determined by the following formula, Serotonin transporter inhibition rate (%)=Average [100×{Average(AUC in the presence of test compound−average AUC in the presence of Escitalopram)/{Average(AUC in the absence of test compound−average AUC in the presence of Escitalopram)}]

This inhibition rate was measured at concentrations of 0.0001 to 10000 nM, and the IC$_{50}$ was calculated.

IC$_{50}$ of paroxetine: 0.6 nM.

IC$_{50}$ of compound of Example 1: 2.4 nM.

Paroxetine and the compound of Example 1 exhibited strong inhibitory effects on serotonin transporters.

Test Example 2

In vivo Efficacy Test by Forced Swimming

The compound of Example 1 (10, 30 or 100 mg/kg) or paroxetine (30 or 100 mg/kg) was administered orally to male BALB/c mice (8-9 mice/group). After 1 hour, the mice were placed individually in glass cylinders (19 cm in height, 9 cm in diameter) holding 9 cm of water, and observed at 23° C. for 6 minutes, during which time their behavior was recorded with a video camera. The control group was given the same amount of vehicle (0.5% methyl cellulose solution, 10 mL/kg).

Measurement Methods

The immobility times during the last 4 minutes were calculated from the video recordings. The mice were considered to be immobile if the following three behavioral criteria were met: they stopped struggling, stopped climbing, and floated on the water basically immobile, with only the slight movement necessary to keep their heads above water.

Results

As shown in FIG. 1, the compound of Example 1 and paroxetine both dose-dependently suppressed immobility time.

Test Example 3

CYP Inhibitory Effects

The CYP inhibitory effects of paroxetine and the compound of Example 1 were tested by the following two methods.

Because time-dependent inhibition of CYP by paroxetine can be evaluated by testing the increase in inhibition after pre-incubation with a solution containing a coenzyme and a human hepatic microsomal fraction containing CYP, a time-dependent inhibition test was performed for the compound of Example 1 as Method 1. Competitive inhibition of CYP was also tested as Method 2.

Method 1

The time-dependent inhibition abilities of paroxetine and the compound of Example 1 were evaluated with respect to five CYP molecules (CYP1A2, 2C9, 2C19, 2D6 and 3A4).

The test substance was added to an enzyme solution (containing human hepatic microsome (0.2 mg/mL), 100 mM Kpi and 0.1 mM EDTA), and pre-incubated for 30 minutes at 37° C. in the presence of or absence of the coenzyme. The final concentration of the test substance was set at 0.1, 0.2, 0.4, 0.5, 1, 2, 10 or 50 μM. A NADPH generating system (60 mM $MgCl_2$ solution containing 3.6 mM β-$NADP^+$, 90 mM glucose-6 phosphate and 1 Unit/mL glucose-6-phosphate dehydrogenase, incubated for 5 minutes to generate NADPH) was used as the coenzyme. After pre-incubation, part of the reaction solution was collected, diluted 10 times by mixing with a model substrate solution and the NADPH generating system, and then incubated for 10 minutes at 37° C. An equal amount of a mixed solution of acetonitrile and methanol (1:1, containing 0.05 μM dextrophan or 0.05 μM propranolol as an internal standard) was added to terminate the reaction, and metabolites of the model substrate in the reaction solution were measured by LC-MS/MS. The model substrates and model substrate metabolites for each CYP enzyme are shown in Table 1. A similar test was also performed with no test substance added as a control test. The ratio relative to the amount of model substrate metabolites in the control test was given as residual activity. The ratio of residual activity in the presence of NADPH relative to residual activity in the absence of NADPH was evaluated, and the ratio of 80% or less was defined "+", while the ratio of above 80% was defined as "−". The results are shown in Table 2.

It can be seen from a comparison of the results of paroxetine and the compound of Example 1 that time-dependent inhibition was reduced by converting the benzodioxol ring to a phthalan ring.

Method 2

Inhibition ability based on competitive inhibition of five CYP enzymes (CYP1A2, 2C9, 2C19, 2D6 and 3A4) was evaluated using paroxetine and the compound of Example 1.

The test substance was added at a final concentration of 1 or 10 μM to an enzyme solution (containing human hepatic microsome (0.2 mg/mL), 100 mM Kpi and 0.1 mM EDTA) containing a model substrate solution, and incubated for 10 minutes at 37° C. in the presence of an NADPH generating system. An equal amount of a mixed solution of acetonitrile and methanol (1:1, containing 0.05 μM dextrophan or 0.05 μM propranolol as an internal standard) was added to terminate the reaction, and metabolites of the model substrate in the reaction solution were measured by LC-MS/MS. The model substrate and model substrate metabolite for each CYP enzyme are shown in Table 3. A similar test was performed without addition of the test substance as a control test. The inhibition rate was determined from the amounts of model substrate metabolites with and without addition of the test substance at each test substance concentration, and the $IC_{50}$ value was calculated from the inhibition rate (calculation method in accordance with Xenobiotica, 1999, 29(1), 53-75). A score of "+" was given if the $IC_{50}$ was 10 μM or less, and "−" if it was greater than 10 μM. The results are shown in Table 4.

It can be seen from a comparison of the results for paroxetine and the compound of Example 1 that inhibition ability was weakened by converting the benzodioxol ring to a phthalan ring.

TABLE 3

Model substrates and model substrate metabolites for CYP enzymes

| CYP isoform | Model substrate | Substrate concentration (μM) | Model substrate metabolite |
| --- | --- | --- | --- |
| CYP1A2 | Phenacetin | 10 | Acetaminophen |
| CYP2C9 | Tolbutamide | 100 | 4-Hydroxytolbutamide |
| CYP2C19 | S-Mephenytoin | 40 | 4'-Hydroxymephenytoin |
| CYP2D6 | Bufuralol | 10 | 1'-Hydroxybufuralol |
| CYP3A4 | Midazolam | 3 | 1'-Hydroxymidazolam |

TABLE 1

Model substrates and model substrate metabolites for each CYP enzyme

| CYP isoform | Model substrate | Substrate concentration (μM) | Model substrate metabolite |
| --- | --- | --- | --- |
| CYP1A2 | Phenacetin | 50 | Acetaminophen |
| CYP2C9 | Tolbutamide | 500 | 4-Hydroxytolbutamide |
| CYP2C19 | S-Mephenytoin | 200 | 4'-Hydroxymephenytoin |
| CYP2D6 | Bufuralol | 50 | 1'-Hydroxybufuralol |
| CYP3A4 | Midazolam | 30 | 1'-Hydroxymidazolam |

TABLE 4

Effect of test substance on CYP enzymes (n = 2)

| Test substance | CYP1A2 | CYP2C9 | CYP2C19 | CYP2D6 | CYP3A4 |
| --- | --- | --- | --- | --- | --- |
| Paroxetine | − | − | − | + | − |
| Example 1 | − | − | − | − | − |

The invention claimed is:

1. A compound represented by formula (1), or a pharmacologically acceptable salt thereof:

TABLE 2

Effect of pre-incubation with human hepatic microsome and test substance on CYP activity (average, n = 2)

| Test substance | Concentration (μM) | CYP1A2 | CYP2C9 | CYP2C19 | CYP2D6 | CYP3A4 |
| --- | --- | --- | --- | --- | --- | --- |
| Paroxetine | 10 | − | − | − | + | − |
|  | 50 | + | − | − | + | + |
| Example 1 | 10 | − | − | − | − | − |
|  | 50 | − | − | − | − | − |

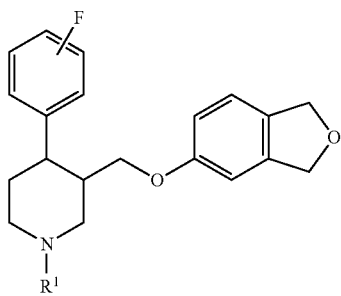

(1)

wherein $R^1$ is a hydrogen atom or $C_{1-6}$ alkyl group.

2. The compound or pharmacologically acceptable salt thereof according to claim 1, wherein $R^1$ is a hydrogen atom.

3. The compound or pharmacologically acceptable salt thereof according to claim 1, wherein the fluorine atom is attached at the para-position with respect to the piperidine ring.

4. (3S,4R)-3-[(1,3-Dihydro-2-benzofuran-5-yloxy)methyl]-4-(4-fluorophenyl) piperidine or a pharmacologically acceptable salt thereof.

5. A pharmaceutical composition comprising the compound or pharmacologically acceptable salt thereof according to claim 1.

6. The pharmaceutical composition according to claim 5, which is a selective serotonin reuptake inhibitor.

7. The pharmaceutical composition according to claim 5, which is an antidepressant agent.

8. The pharmaceutical composition according to claim 5, which is an agent for the treatment of premature ejaculation.

9. A method of selectively inhibiting serotonin reuptake comprising administering the compound or pharmacologically acceptable salt thereof according to claim 1 to a patient.

10. A method of treating depression comprising administering the compound or pharmacologically acceptable salt thereof according to claim 1 to a patient.

11. A method of treating premature ejaculation comprising administering the compound or pharmacologically acceptable salt thereof according to claim 1 to a patient.

\* \* \* \* \*